(12) United States Patent
LeBlanc et al.

(10) Patent No.: US 10,011,820 B2
(45) Date of Patent: Jul. 3, 2018

(54) ADIPOSE STROMAL VASCULAR FRACTION CELL CONSTRUCTS

(71) Applicant: UNIVERSITY OF LOUISVILLE RESEARCH FOUNDATION, INC., Louisville, KY (US)

(72) Inventors: Amanda J. LeBlanc, Louisville, KY (US); James B. Hoying, Louisville, KY (US); Stuart K. Williams, Harrods Creek, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 501 days.

(21) Appl. No.: 14/348,584

(22) PCT Filed: Oct. 1, 2012

(86) PCT No.: PCT/US2012/058378
§ 371 (c)(1),
(2) Date: Mar. 28, 2014

(87) PCT Pub. No.: WO2013/049862
PCT Pub. Date: Apr. 4, 2013

(65) Prior Publication Data
US 2014/0242143 A1 Aug. 28, 2014

Related U.S. Application Data

(60) Provisional application No. 61/542,105, filed on Sep. 30, 2011.

(51) Int. Cl.
*C12N 5/071* (2010.01)
*A61K 35/34* (2015.01)
*A61K 35/35* (2015.01)

(52) U.S. Cl.
CPC .............. *C12N 5/069* (2013.01); *A61K 35/34* (2013.01); *A61K 35/35* (2013.01)

(58) Field of Classification Search
None
See application file for complete search history.

(56) References Cited

U.S. PATENT DOCUMENTS

2008/0226726 A1  9/2008  Jaconi et al.
2010/0124563 A1  5/2010  Coleman et al.

OTHER PUBLICATIONS

Bolooki et al., Acute Myocardial Infarction, Cleveland Clinic, published: Aug. 2010.*
International Search Report in PCT/US12/58378, Lee W. Young, US International Searching Authority, Alexandria VA, dated Dec. 11, 2012.
Written Opinion of the International Searching Authority in PCT/US12/58378, Lee W Young, US International Searching Authority, Alexandria VA, dated Dec. 11, 2012.
Badylak S, Obermiller J, Geddes L, and Matheny R. Extracellular matrix for myocardial repair. Heart Surg Forum 6: E20-26, 2003.
Barandon L, Couffinhal T, Dufourcq P, Alzieu P, Daret D, Deville C, and Duplaa C. Repair of myocardial infarction by epicardial deposition of bone-marrow-cell-coated muscle patch in a murine model. Ann Thorac Surg 78: 1409-1417, 2004.
Derval N, Barandon L, Dufourcq P, Leroux L, Lamaziere JM, Daret D, Couffinhal T, and Duplaa C. Epicardial deposition of endothelial progenitor and mesenchymal stem cells in a coated muscle patch after myocardial infarction in a murine model. Eur J Cardiothorac Surg 34: 248-254, 2008.
Feldman LJ, Himbert D, Juliard JM, Karrillon GJ, Benamer H, Aubry P, Boudvillain O, Seknadji P, Faraggi M, and Steg G. Reperfusion syndrome: relationship of coronary blood flow reserve to left ventricular function and infarct size. J Am Coll Cardiol 35: 1162-1169, 2000.
Hamdi H et al, Epicardial adipose stem cell sheets results in greater post-infarction survival than intramyocardial injections, Cardiovasc Res 91: 483-491, 2011.
Hofmann M, Wollert KC, Meyer GP, Menke A, Arseniev L, Hertenstein B, Ganser A, Knapp WH, and Drexler H. Monitoring of bone marrow cell homing into the infarcted human myocardium. Circulation 111: 2198-2202, 2005.
Huang W, Zhang D, Millard RW, Wang T, Zhao T, Fan GC, Ashraf A, Xu M, Ashraf M, and Wang Y. Gene manipulated peritoneal cell patch repairs infarcted myocardium. J Mol Cell Cardiol 48: 702-712.
Kellar RS, Shepherd BR, Larson DF, Naughton GK, and Williams SK. Cardiac patch constructed from human fibroblasts attenuates reduction in cardiac function after acute infarct. Tissue Eng 11: 1678-1687, 2005.
Leor J, Aboulafia-Etzion S, Dar A, Shapiro L, Barbash IM, Battler A, Granot Y, and Cohen S. Bioengineered cardiac grafts: A new approach to repair the infarcted myocardium? Circulation 102:lll56-61, 2000.
Lu WN, Lu SH, Wang HB, Li DX, Duan CM, Liu ZQ, Hao T, He WJ, Xu B, Fu Q, Song YC, Xie XH, and Wang CY. Functional improvement of infarcted heart by co-injection of embryonic stem cells with temperature-responsive chitosan hydrogel. Tissue Eng Part A 15: 1437-1447, 2009.
Ragosta M, Powers ER, Samady H, Gimple LW, Sarembock IJ, and Beller GA. Relationship between extent of residual myocardial viability and coronary flow reserve in patients with recent myocardial infarction. Am Heart J 141: 456-462, 2001.
Resnic FS et al., No-reflow is an independent predictor of death and myocardial infarction after percutaneous coronary intervention, Am Heart J 145: 42-46, 2003.
Shan, T., Liu, W. and Kuang, S.; "Fatty acid binding protein 4 expression marks a population of adipocyte progenitors in white and brown adipose tissues", FASEB J. Jan. 2013; 27(1): 277-287.
Tchoukalova Y. D., Sarr M. G., Jensen M. D.; "Measuring committed preadipocytes in human adipose tissue from severely obese patients by using adipocyte fatty acid binding protein", Am. J. Physiol. Regul. Integr. Comp. Physiol. 287 (5), R1132-40. Epub Jul. 29, 2004.
Marvin E. Morris, et al; "Systemically Delivered Adipose Stromal Vascular Fraction Cells Disseminate to Peripheral Artery Walls and Reduce Vasomotor Tone Through a CD11b+ Cell-Dependent Mechanism"; Stem Cells Translational Medicine, 2015; 4:1-12.

* cited by examiner

*Primary Examiner* — Michael G Hartley
*Assistant Examiner* — Nabila G Ebrahim
(74) *Attorney, Agent, or Firm* — Conley Rose, PC

(57) ABSTRACT

Three-dimensional tissue constructs are described, which may be created by isolating adipose-derived stromal vascular fraction (SVF) cells, plating the cells onto a polymer scaffold, and culturing the plated scaffold in a culture of DMEM with approximately 10% FBS.

14 Claims, 16 Drawing Sheets

| Hemodynamic Parameter | Sham | MI | MI SVF | MI Vicryl |
|---|---|---|---|---|
| HR (min$^{-1}$) | 279.5±23.1 | 261.5±23.1 | 259.4±12.2 | 245.8±34.2 |
| CO(mL/min) | 34.3±2.0 | 23.8±4.8 | 27.6±1.8 | 16.6±3.4* |
| ESP(mmHg) | 97.1±7.3 | 108.1±6.5 | 99.3±9.3 | 102.8±8.2 |
| EDP(mmHg) | 5.4±0.5 | 6.0±0.9 | 5.5±0.7 | 4.1±0.5 |
| ESV(μL) | 42.2±8.5 | 166.9±27.6*† | 63.8±9.2 | 181.1±27.6*† |
| EDV(μL) | 162.7±17.1 | 242.3±17.3† | 152.3±14.1 | 243.2±32.6† |
| SV(μL) | 124.8±11.2 | 90.1±16.0 | 107.5±8.8 | 73.0±19.4 |
| EF(%) | 76.2±3.7 | 37.0±8.0*† | 65.6±4.1 | 28.6±6.2*† |

*FIG. 5B*

ADIPOSE STROMAL VASCULAR FRACTION CELL CONSTRUCTS

PRIORITY

This application is a national phase of International Application No. PCT/US2012/058378, filed on Oct. 1, 2012, which claims priority to U.S. Provisional Application No. 61/542,105, filed Sep. 30, 2011, the disclosures of which are hereby incorporated herein by reference in their entireties.

GOVERNMENT RIGHTS

The United States Government may have certain rights in this application pursuant to Grant EB007556 (JBH and SKW) awarded by the National Institute of Health.

TECHNICAL FIELD

This subject matter relates generally to creating three-dimensional tissue constructs using adipose-derived stromal vascular fraction cells.

BACKGROUND

Following a myocardial infarction (MI), impaired microvascular blood flow (BF) results in loss of cardiomyocyte function and, if untreated, can lead to widespread left ventricular (LV) contractile failure. Protecting the integrity and function of the microcirculation following MI remains a major target of cardiac regenerative medicine in order to prevent the progressive dysfunctional pathological changes that lead to eventual myocardial necrosis. The extent of unviable myocardium within an infarct region after coronary vessel occlusion depends on several factors, including time to reperfusion, collateral vessel development potential, and possible ischemic preconditioning. See Ragosta M, Powers E R, Samady H, Gimple L W, Sarembock I J, and Beller G A. Relationship between extent of residual myocardial viability and coronary flow reserve in patients with recent myocardial infarction. *Am Heart J* 141: 456-462, 2001. The most traditional clinical treatment for acute MI is coronary revascularization of the infarct-related artery, specifically percutaneous coronary intervention (PCI), thrombolysis, or bypass surgery. However, as many as 48% of PCI patients do not regain distal microvascular perfusion even though the suspect artery is angiographically open. See Feldman L J, Himbert D, Juliard J M, Karrillon G J, Benamer H, Aubry P, Boudvillain O, Seknadji P, Faraggi M, and Steg G. Reperfusion syndrome: relationship of coronary blood flow reserve to left ventricular function and infarct size. *J Am Coll Cardiol* 35: 1162-1169, 2000. As such, there is a clinical need for treatments that are developed specifically with regard to coronary microcirculatory development, maintenance, and repair.

Recent approaches to treat ischemia have focused on injection of suspensions of regenerative therapies including direct injection of growth factors, cytokines, and/or progenitor cells. Cellular therapy has been limited by lack of retention of injected cells, as only ~1.3-2.6% of transplanted cells are retained in the infarcted myocardium after intracoronary injection. See Hofmann M, Wollert K C, Meyer G P, Menke A, Arseniev L, Hertenstein B, Ganser A, Knapp W H, and Drexler H. Monitoring of bone marrow cell homing into the infarcted human myocardium. *Circulation* 111: 2198-2202, 2005. Additionally, a recent study by Hamdi H et al, Epicardial adipose stem cell sheets results in greater post-infarction survival than intramyocardial injections, *Cardiovasc Res* 91: 483-491, 2011, showed that an adipose cell sheet implant resulted in greater post-infarct survival and greater cell engraftment than intramyocardial injections of the same cells. Therefore, more approaches have begun to focus on a combination of cell therapy and scaffolds to address the inadequate retention, survival, and integration of injected cells into the host tissue. Cellular and acellular cardiac patches (Badylak S, Obermiller J, Geddes L, and Matheny R. Extracellular matrix for myocardial repair. *Heart Surg Forum* 6: E20-26, 2003; Kellar R S, Shepherd B R, Larson D F, Naughton G K, and Williams S K. Cardiac patch constructed from human fibroblasts attenuates reduction in cardiac function after acute infarct. *Tissue Eng* 11: 1678-1687, 2005; Leor J, Aboulafia-Etzion S, Dar A, Shapiro L, Barbash I M, Battler A, Granot Y, and Cohen S. Bioengineered cardiac grafts: A new approach to repair the infarcted myocardium? *Circulation* 102: 11156-61, 2000) as well as injectable in situ gelling materials (Lu W N, Lu S H, Wang H B, Li D X, Duan C M, Liu Z Q, Hao T, He W J, Xu B, Fu Q, Song Y C, Xie X H, and Wang C Y. Functional improvement of infarcted heart by co-injection of embryonic stem cells with temperature-responsive chitosan hydrogel. *Tissue Eng Part A* 15: 1437-1447, 2009) have all been explored for use as cardiac repair therapies focused on rebuilding myocardial tissue and/or microcirculatory repair. For example, muscle patches paired with genetically engineered mesenchymal stem cells (MSC) (Huang W, Zhang D, Millard R W, Wang T, Zhao T, Fan G C, Ashraf A, Xu M, Ashraf M, and Wang Y. Gene manipulated peritoneal cell patch repairs infarcted myocardium. *J Mol Cell Cardiol* 48: 702-712), progenitor cells combined with MSCs (Derval N, Barandon L, Dufourcq P, Leroux L, Lamaziere J M, Daret D, Couffinhal T, and Duplaa C. Epicardial deposition of endothelial progenitor and mesenchymal stem cells in a coated muscle patch after myocardial infarction in a murine model. *Eur J Cardiothorac Surg* 34: 248-254, 2008), and bone marrow cells in a collagen matrix (Barandon L, Couffinhal T, Dufourcq P, Alzieu P, Daret D, Deville C, and Duplaa C. Repair of myocardial infarction by epicardial deposition of bone-marrow-cell-coated muscle patch in a murine model. *Ann Thorac Surg* 78: 1409-1417, 2004) have all been somewhat effective at improving overall heart function after MI when compared to untreated hearts. Although increasing viable myocardial tissue remains critical to post-MI hearts, another major component of treatment should focus on coronary microcirculatory repair in order to supply adequate blood flow to transplanted cardiomyocytes.

BRIEF SUMMARY

The present disclosure relates to various methods and structures. A three-dimensional tissue construct may be created using adipose-derived stromal vascular fraction (SVF) cells.

In one embodiment, a method is presented for preparing a three dimensional tissue construct for use in treating a patient, comprising isolating adipose-derived stromal vascular fraction cells from a sample of adipose tissue, plating the cells into a polymer scaffold, and culturing the plated scaffold in a culture of DMEM with approximately 10% FBS. Preferably, the scaffold comprises polyglycolic acid.

In another embodiment a method for treating an animal suffering from acute myocardial infarction, the animal comprising an infarct region comprising an epicardial surface is provided, comprising preparing a construct as described above, and suturing the construct directly onto the epicardial surface. Preferably, this suturing takes place within 8 hours of the onset of the acute myocardial infarction.

Various additional embodiments, including additions and modifications to the above embodiments, are described herein.

BRIEF DESCRIPTION OF THE DRAWINGS

The accompanying drawings, which are incorporated into and constitute a part of this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted based on the text of the specification or the common knowledge within this field.

In the drawings:

FIG. 1 shows an SVF construct characterization and description.

FIG. 3 shows an evaluation of vessel count and microvascular perfusion in the area at risk.

FIG. 5 shows heart function as determined by pressure-volume relationship. FIG. 5B is a summary of cardiac functional parameters. Sham and MI SVF hearts display similar heart function and PV relationship. Hearts from MI and MI Vicryl exhibit a rightward shift in PV relationship and decreased EF due to altered ESV and EDV compared to Sham and MI SVF. An asterisk (*) indicates significant difference from Sham. A cross (†) indicates significant difference from MI SVF. N≥4 rats/group, P≤0.05.

FIG. 6 shows a histological evaluation of hearts to determine infarct size following treatment.

DETAILED DESCRIPTION

Figure 1A:
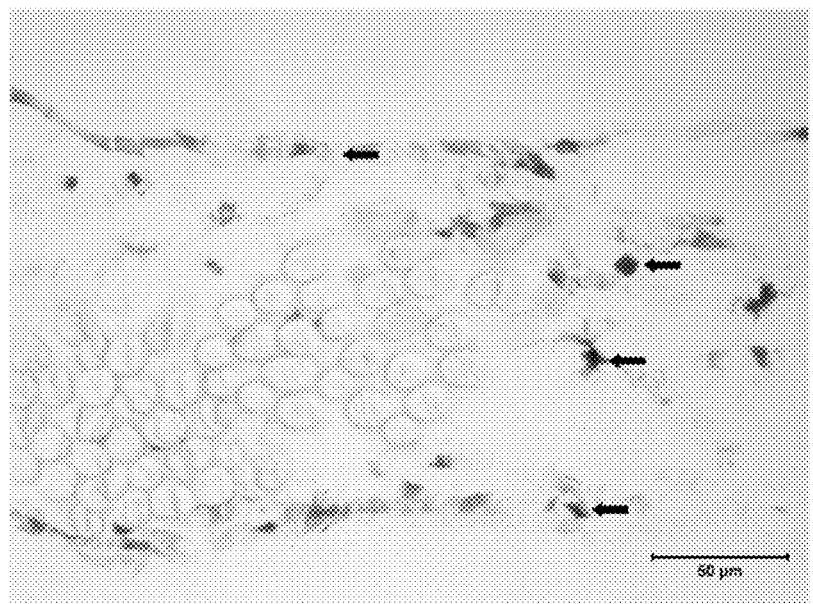
FIG. 1A shows a cross sectional H&E stain of the SVF construct after culture for 14 days. Arrows indicate cells present throughout depth of construct.

Various example embodiments of the present inventions are described herein in the context of preparing adipose stromal vascular fraction cell constructs.

Those of ordinary skill in the art will understand that the following detailed description is illustrative only and is not intended to be in any way limiting. Other embodiments of the present inventions will readily suggest themselves to such skilled persons having the benefit of this disclosure, in light of what is known in the relevant arts.

Not all of the routine features of the exemplary implementations described herein are shown and described. In the development of any such actual implementation, numerous implementation-specific decisions must be made in order to achieve the specific goals of the developer, such as compliance with regulatory, safety, social, environmental, health, and business-related constraints, and that these specific goals will vary from one implementation to another and from one developer to another. Moreover, such a developmental effort might be complex and time-consuming, but would nevertheless be a routine undertaking of engineering for those of ordinary skill in the art having the benefit of this disclosure.

As embodied herein, a significant angiogenic response associated with the implantation of tissue-engineered patches directly onto the epicardial surface may be demonstrated. Specifically, a marked angiogenic response and improved cardiac function can be evoked by placing a construct of viable Dermagraft (a tissue-engineered Vicryl patch containing human dermal fibroblasts) onto the epicardial surface of a mouse heart that may be subjected to regional ischemic damage. Dermagraft elicits angiogenesis at the site of ischemic injury by secreting a myriad of angiogenic growth factors, such as vascular endothelial growth factor (VEGF), hepatocyte growth factor (HGF), and transforming growth factor $\beta_1$ (TGF$\beta_1$). Implanting this three-dimensional fibroblast matrix onto the epicardial surface of the heart post-MI resulted in smaller LV infarct size and improved LV function after treatment. In addition, our laboratory has previously designed peripheral constructs to promote vascularization using isolated adipose-derived microvessel fragments. Indeed, both of these tissue-engineered treatments can deliver promising results in terms of expanding the coronary microvasculature and lessening cardiac malfunction after MI; however, we believe the potential for an autograft cell construct application in the treatment of MI would be a superior therapy due to the limitation and/or elimination of tissue inflammation and rejection.

Contained within adipose tissue is a regenerative, heterogeneous cell population defined as the stromal vascular fraction (SVF), consisting of endothelial cells, smooth muscle cells, blood cells and mesenchymal cells. SVF cells exhibits the potential to differentiate into various mesodermic lineages and demonstrates desirable characteristics as a cell population candidate for myocardial injury cell therapy. Therefore, our objective was to assess the coronary microcirculatory response of post-infarcted cardiac tissue to a degradable construct laden with adipose-derived SVF cells and to determine whether such a response is associated with a clinically significant improvement in cardiac performance. We hypothesized that a SVF cell construct implanted immediately after MI would help increase coronary perfusion in the infarct region, thereby improving overall cardiac function compared with untreated MI hearts.

Methods

Stromal Vascular Fraction Isolation

Green fluorescent protein (GFP)-tagged adult male Sprague Dawley rats (Rat Research and Resource Center, University of Missouri, Columbia, Mo.) were put under anesthesia (Ketamine 40-80 mg/kg and Xylazine 5-10 mg/kg). GFP+SVF cells were isolated from epididymal fat pads. Harvested fat pads were washed in 0.1% BSA-PBS, finely minced and digested in 2 mg/ml Type I collagenase solution for 40 min at 37° C. with vigorous shaking. Buoyant adipocytes were removed by centrifugation and the entire cell pellet suspended in 0.1% BSA-PBS. Cells were immediately plated ($1 \times 10^6$ cells/cm$^2$) onto a piece of polyglycolic acid (Vicryl™) 1×1.5 cm, and cultured for 14 days in DMEM with 10% FBS.

Myocardial Infarction and Construct Implantation

All animal surgeries were performed in accordance with protocols approved by the University of Louisville animal review committee and the National Institutes of Health (NIH). After anesthesia was introduced (Isoflurane 1-3%-O$_2$ balance) and lack of toe pinch reflex was observed, the heart was exposed through a left lateral thoracotomy. Sham animals were sutured close in 3 layers and allowed to recover. Infarcts were performed by left anterior descending (LAD) artery ligation with 7-0 nylon suture (Ethicon) and confirmed via visualization of blanched tissue distal to the ligation site. Infarcted animals were immediately randomized into one of the 3 treatment groups (MI only, MI Vicryl, or MI SVF). A SVF construct was sewn directly onto the area of blanching for the MI SVF group (see below for details). MI Vicryl rats received a Vicryl only implant (no cells). The chest was closed in 3 layers, allowed to recover and given Buprinorphine (0.05 mg/kg) every 8-12 hrs for the next 48 hrs.

Endpoint parameters were assessed 4 weeks after surgery following injection of anesthesia (Ketamine 40-80 mg/kg and Xylazine 5-10 mg/kg) and confirming lack of toe pinch reflex. Rats were euthanized by removal of the heart.

Construct Surgical Implantation

Figure 1B:
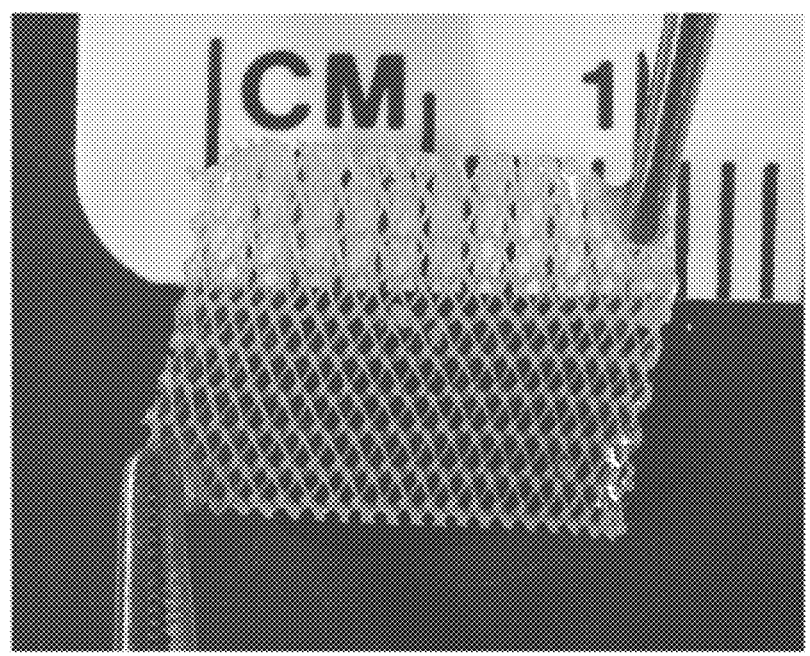
FIG. 1B shows a photograph of the SVF cell construct prior to implant.
Figure 1C:
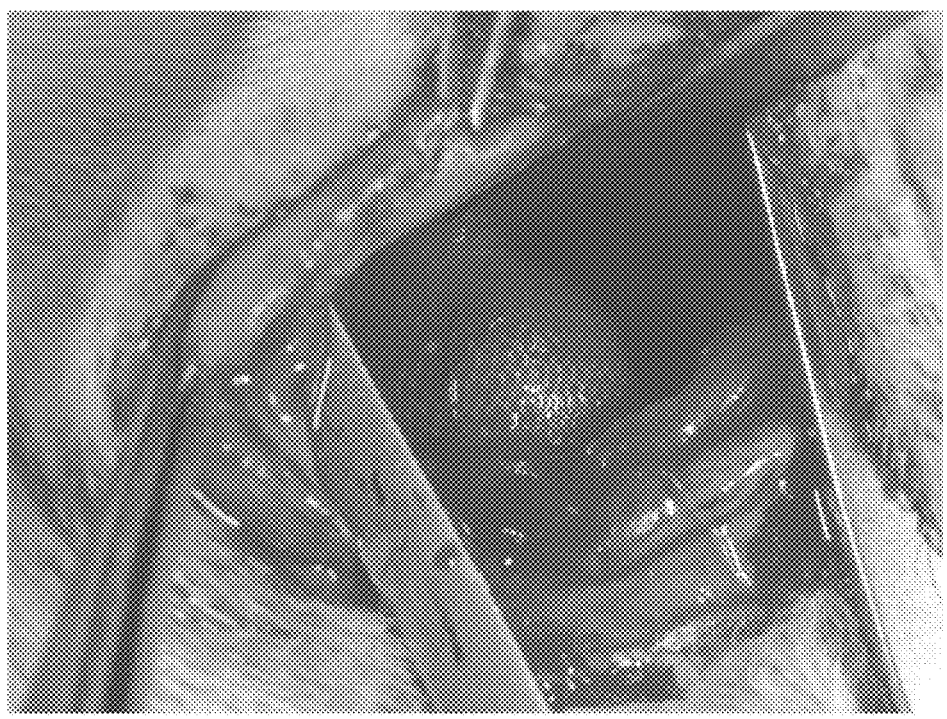
FIG. 1C shows an image of the SVF construct sutured on to the epicardial wall after MI was performed.

After ligating the LAD and confirming distal blanching of the myocardial tissue, the SVF construct was removed from the incubator (FIG. 1B, 37° C., 5% CO$_2$) and placed directly on the epicardial surface. The SVF construct was malleable to the curvature of the heart and completely covered the area of infarct, overlapping slightly into the proximal non-infarct region (FIG. 1C). A single 7-0 silk suture was sewn immediately distal to the LAD occlusion site to minimize blood loss while securing the SVF construct to the epicardial surface.

Left Ventricular Function Assessment—PV Loop Analysis

Analysis of pressure-volume (PV) loop relationships of the LV utilized the Millar conductance system and was performed according to methods described in Shepherd B R, Hoying J B, and Williams S K, Microvascular transplantation after acute myocardial infarction, Tissue Eng., 13:2871-2879, 2007. At the time of assessment, rats were anesthetized with an injection of Ketamine (40-80 mg/kg) and Xylazine (5-10 mg/kg). A substernal transverse incision to expose the inferior vena cava (IVC) was performed. An apical stab was used for catheter insertion and positioned along the cardiac longitudinal axis with the distal electrode in the aortic root and the proximal electrode in the LV apex. Placement of the catheter was monitored directly. Overall LV function was assessed by collecting heart rate (HR), end-systolic pressure (ESP), end-diastolic pressure (EDP), ejection fraction (EF), stroke volume (SV), end-systolic volume (ESV), end-diastolic volume (EDV), and CO under baseline conditions, following transient inferior vena cava (IVC) occlusion (to assess contractility and LV stiffness), and after intravenous administration of 20-40 ul of 30% saline (for conductance volume calibration).

Myocardial Blood Flow Assessment

For each measurement, $1.2 \times 10^6$ nonradioactive elementally labeled 15-um microspheres (Worcester, Mass., Biopal) were injected into the left ventricle transapically while simultaneously sampling carotid blood at a known withdrawal rate. This dose is well below the amount of spheres necessary to cause physiologic effects in the heart, an estimate suggests that several grams of microspheres are needed to induce physiological effects. Two separate isotopes were injected transapically into the rat at the terminal point in the study (at 4 weeks post-surgery): one at baseline and the other during a 5-minute intravenous dobutamine injection (10 ug/kg/min). Dobutamine is one of the most potent inotropes and is a cardioselective β-adrenoreceptor agonist and is often used in stress tests to detect the presence of hibernating myocardium in clinical chronic myocardial ischemia. The LV was harvested, sectioned into 4 radial slices from the apex to papillary muscle, and all but the apex was quartered. This sectioning allows us to analyze blood flow in specific regions of the LV (i.e. infarcted area, peri-infarcted region, septal wall). Sections and blood samples were sent to BioPal (Worcester, Mass.) for neutron activation, which is capable of simultaneously detecting a single microsphere in a variety of labeled isotopes in an intact myocardial sample.

BF (ml/min/g)=[(Withdrawal rate of blood sample [ml/min]*dpm from tissue)/(dpm from blood sample)]/tissue weight (g), where dpm represents disintegrations per minute. Withdrawal rate of blood sample was set at 500 µl/min for 2 minutes. Coronary BF reserve was calculated within each animal as % of baseline BF by the following equation:

BF reserve (%)=(Dobutamine BF−Baseline BF)/(Baseline BF)*100.

Histology and Immunohistochemistry

Construct histology was accomplished by fixing constructs processing into paraffin. 5-6 µm thick cross sections were stained with hematoxylin and eosin (H&E). General histological structure of the heart was determined on deparaffinized, 5-6 µm thick sections stained with Masson's Trichrome. Infarct regions were manually traced and represented as percent of total LV area. Vascular endothelial cells were identified using a rodent-specific lectin, GS-1 (*Griffonia simplicifolia* I). Vessel density was determined by counting discrete, GS-1 positive structures from infarcted sections or area at risk (approximately 1 mm proximal to the apex on free wall of LV). In each animal, 5 discrete, random images (20× magnification) from the infarct region or area at risk were counted for GS-1+ structures. For each image, the vessel count was divided by the area (mm$^2$), resulting in count/mm$^2$. The total sum of count/mm$^2$ was divided by 5 (images/animal) in order to get the average count/mm$^2$/animal. The count/mm$^2$/animal was then averaged for each group.

To verify the presence of engrafted GFP+ cells in MI SVF hearts, hearts were explanted four weeks post-surgery and retroperfused with 4% PFA and 30% sucrose solutions, fixed in Tissue-Tek (Sakura), and frozen in liquid-nitrogen-cooled isopentane. Prior to immunostaining, hearts were sliced into 20 µm thick cross sections using an ultramicrotome (Leica) approximately 2 mm proximal to the apex. GFP+SVF cells were identified in the infarct area using an antibody directed against GFP (1:100, Invitrogen), while negative controls were incubated with rabbit isotype control (1:100, Invitrogen). Primary antibody was detected by incubating the section with FITC-conjugated anti-rabbit IgG (1:100). Non-specific binding fluorescence of negative control slides was subtracted from the remainder of GFP+ immunostained slides. In addition, endothelial cell-comprised vessels were identified using rhodamine-labeled GS-1 (1:250, Vector Labs).

Quantitative Real-Time Polymerase Chain Reaction (PCR)

Cells from 14-day cultured SVF constructs were isolated from the Vicryl scaffold by a cell dissociation enzyme to determine what genes are upregulated in the SVF construct prior to implant. Total RNA from SVF patches was isolated using the RNeasy mini kit (Qiagen) after SVF cells were extracted from Vicryl using Trypsin (1:10 dilution). To determine alterations in gene transcription following treatment with SVF construct, LV RNA was isolated from the infarct region in both MI and MI SVF groups by homogenization, following with alcohol precipitation. Genes were chosen based on 5 categories deemed important in potential mechanism of SVF construct action, such as promatrix (Fibronectin [Fn1] and Laminin 5 [Ln5)), proangionenic (Hgf and Vegfa), stem cell recruiting (Sdf1 and Ckit), proinflammatory (Cxcr4 and Tnfα), and vasoactivity (eNOS [Nos3] and TxA$_2$ [Tbxa2r]). Gene primer sets are shown in Table 1. RNA analysis was performed using ΔΔCt method. Expression of each target m relative to Dynactin was calculated based on threshold cycle (Ct)=$2^{-\Delta(\Delta Ct)}$, where $\Delta Ct=Ct_{target}-Ct_{Dynactin}$. RNA expression for MI SVF was made relative to MI only infarct area using the following equation: $\Delta(\Delta Ct)=\Delta Ct_{MI\ only}-\Delta Ct_{MI+SVF}$.

Flow Cytometric Analysis

Phenotype of cells isolated from SVF constructs was determined by assessing their surface markers using flow cytometric analysis. Cells were enzymatically released from 14-day cultured SVF constructs using Trypsin (GIBCO). Antibodies included CXCR4 (a receptor for SDF-1), CD68 (typical macrophage marker), CD45 (leukocyte common antigen), IL-4R (Interleukin 4 Receptor), MHC Class II (major histocompatibility complex typically found on macrophages), PDGF-Rβ (growth factor that acts as a mitogen for cells of mesenchymal origin), VE-Cadherin (adhesion and angiogenesis), and VEGF-R2 (angiogenesis). Positive rate was calculated as % of events above isotype control for that particular antibody, and were averaged with three measurements for each surface marker.

Statistical Analysis

Mean differences between groups in all PV loop parameters, infarct size, BF, coronary BF reserve, and vessel count were determined by ANOVA calculation. Post-hoc analysis was determined by Tukey's test where appropriate.

Results

Figure 1D:
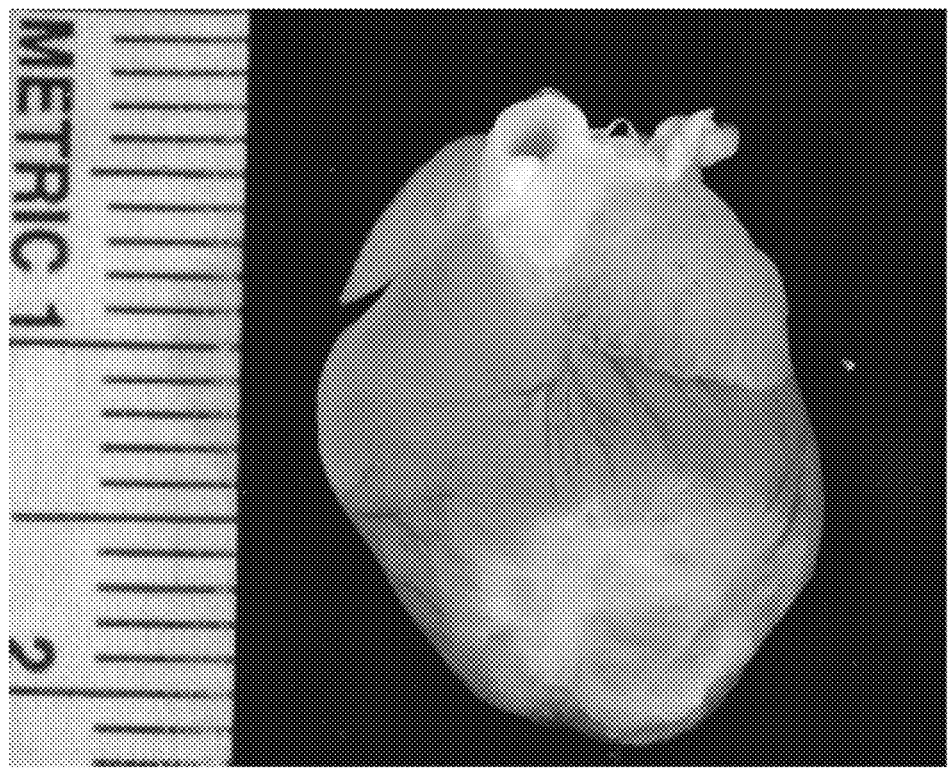
FIG. 1D shows a 28 day MI+SVF patch heart explant, demonstrating most of the Vicryl mesh of the SVF construct has degraded and left a collagen rich outermost layer.
Figures 7A, 7B:
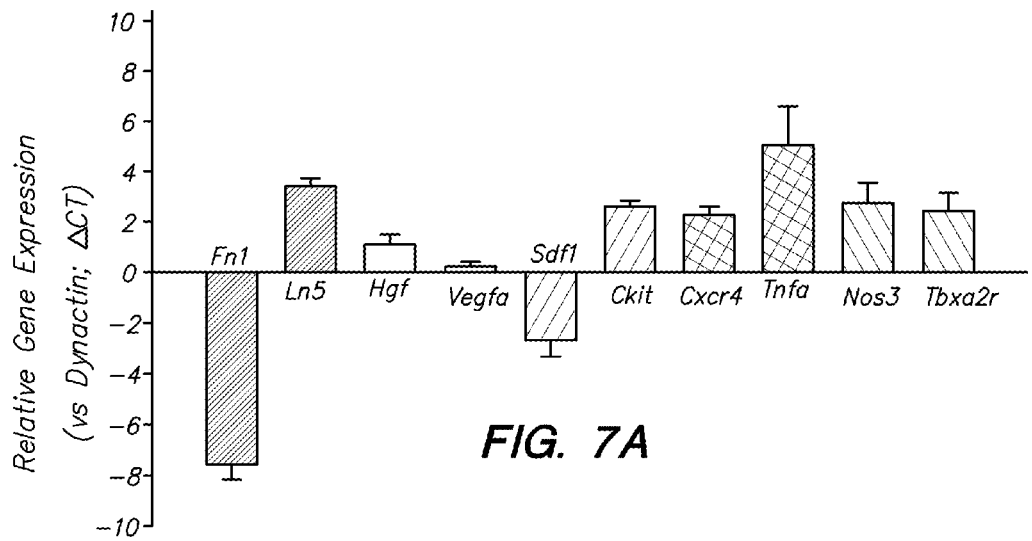
FIG. 7A shows RNA expression from cells on the 14-day cultured SVF construct (N=4).
FIG. 7B shows a flow cytometric analysis of SVF construct cells prior to implant. The positive (%) were averaged from three separate measurements for each surface marker and represent % events above isotype control. Values are mean±SE.

Characterization of SVF Construct, LV Infarct Area Following Construct Implantation We wanted to further characterize the SVF construct in order to identify potential signaling mechanisms and to compare gene expression to previous epicardial patches. H&E stain of a cross section of the SVF construct prior to implant demonstrate cells throughout the depth of the construct, indicating that the 14-day culture time allows cells to disperse and are not localized to one side (FIG. 1A). FIGS. 1B and 1C show the construct prior to implant and immediately after implantation on the epicardial surface, respectively. FIG. 1D shows the explanted heart 30 days after MI+SVF construct implant. To better characterize gene expression of the SVF construct, we assessed both gene transcript and phenotypic surface markers of the 14-day cultured SVF construct by RNA and FACS analysis. Isolated cells from the SVF construct demonstrated higher gene expression in Ln5, Ckit, Cxcr4, Tnfα, Nos3 and Tbxa2r, while gene expression for Fn1 and Sdf1 were decreased (FIG. 7A). FACS analysis revealed that SVF construct cells exhibit 76.0±1.6% positive rate for CD68, a macrophage marker, and 31.3±2.3% positive rate for VEGFR2, an angiogenic receptor marker (FIG. 7B).

Heart Remodeling and Fibrosis Following Post-MI Treatment

Histologic evaluation of hearts that were implanted immediately with SVF construct after ligation showed greater muscle fibers and less collagen and fibrosis than MI and MI Vicryl hearts (FIGS. 6 A&B). However, ANOVA comparisons between means did not reach threshold for statistical significance (P=0.074 for MI vs MI SVF and P=0.060 for MI vs MI Vicryl, FIG. 3C). This may be due to a decrease in LV free wall thickness in the area of infarct in both the MI and MI Vicryl groups, resulting in lower infarct % of total LV area than what Masson's Trichrome stained images exhibit (FIG. 6A). To establish whether specific genes thought to be involved in improving heart function and angiogenesis were affected by SVF construct implantation, we measured gene expression (ΔΔCt) in the infarcted tissue from hearts after 4 weeks without treatment (MI) and with the SVF construct (MI SVF). MI+SVF infarct area exhibited more than a 4-fold increase in expression of SDF-1 and a 2.9-fold increase in eNOS compared to MI only. Expression for Fibronectin (2.3-fold), TxA$_2$ receptor (0.5-fold), and CXCR4 (0.2-fold) were also increased in MI+SVF tissue compared to untreated MI only hearts. SVF construct placement at time of ligation resulted in negative fold changes in gene expression of Laminin 5, HGF, ckit, and TNFα in LV infarct tissue after 4 weeks (FIG. 6D).

Impact of Construct Implantation on Overall Heart Function

Figure 5A:
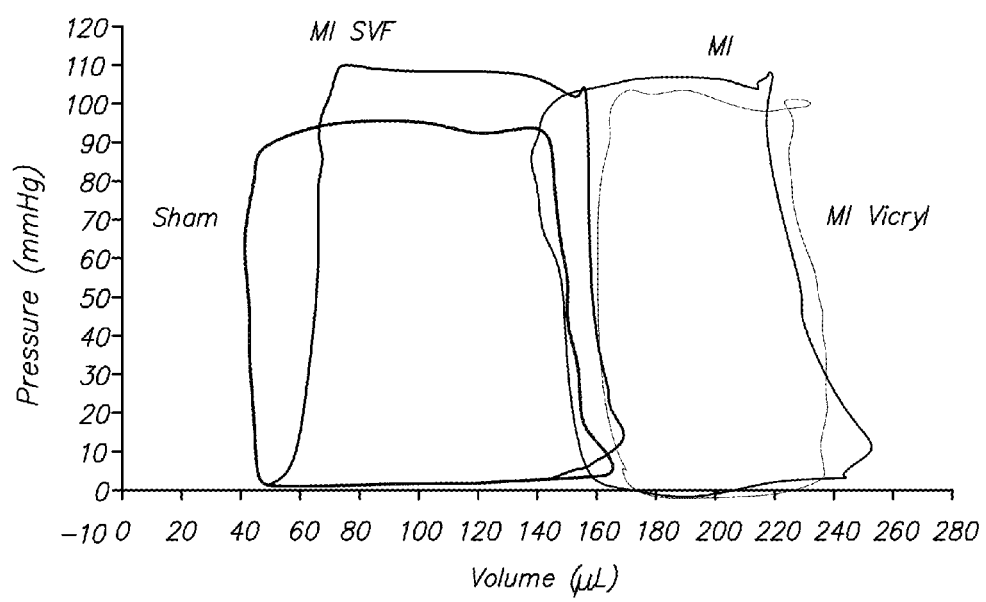
FIG. 5A shows representative single PV loop recording during baseline.
Figure 6A:
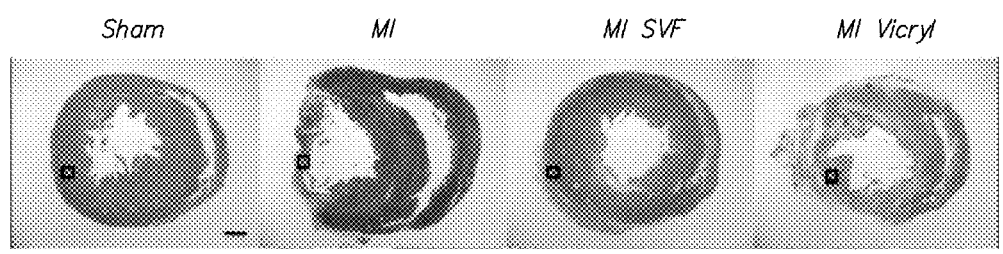
FIG. 6A shows Masson's Trichrome stain, cross sectioned approximately 5 mm proximal to apex, scale bar=1 mm.
Figure 6B:
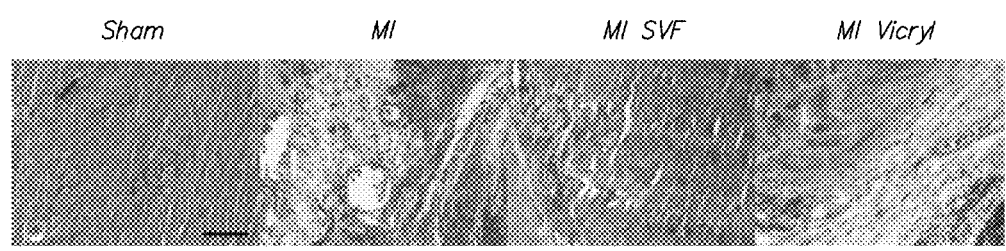
FIG. 6B shows a higher magnification from inset, scale bar=100 μm. MI and MI Vicryl exhibit thinner LV free walls and more fibrosis (more blue in outer LV wall) throughout infarct area compared to MI SVF.
Figure 6C:
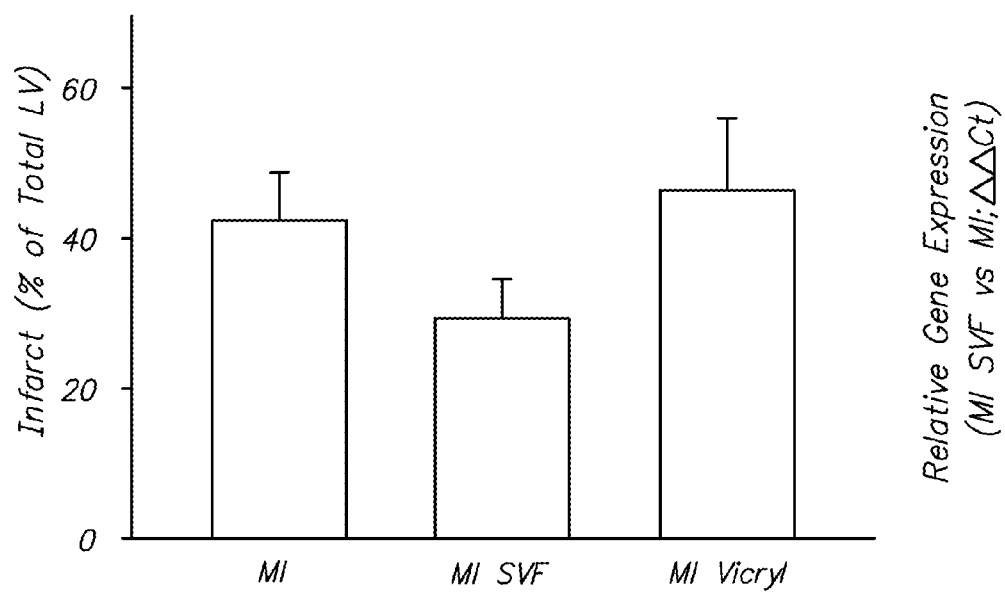
FIG. 6C shows treatment with SVF construct results in less infarct % of total LV area compared to MI and MI Vicryl.
Figure 6D:
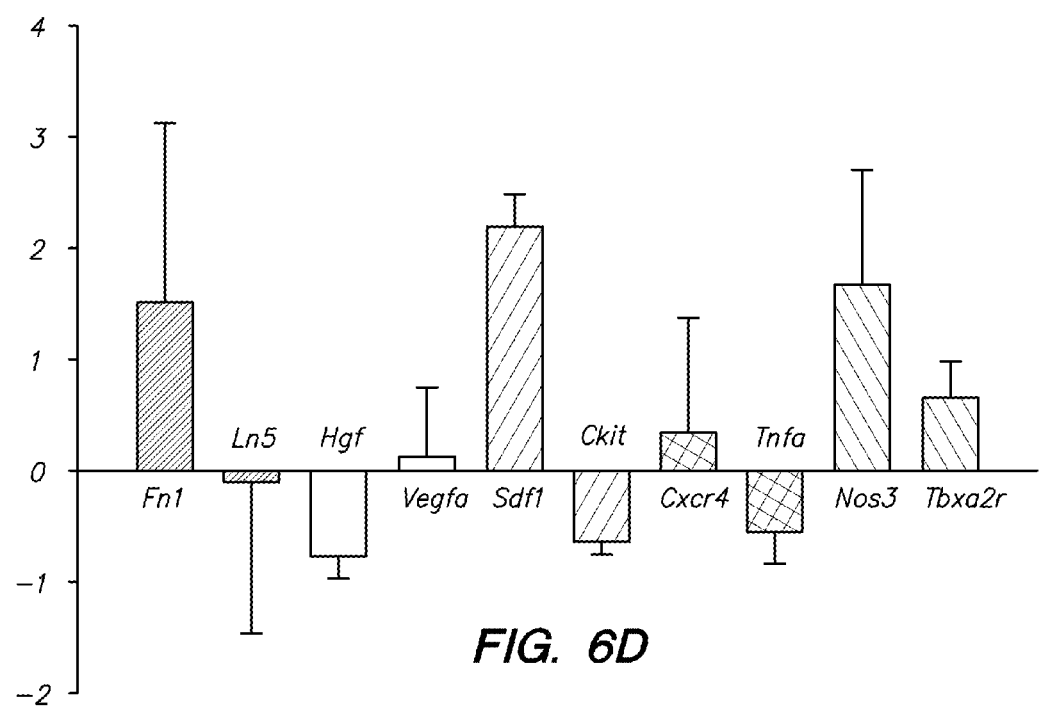
FIG. 6D shows quantitative real-time PCR of target gene expression in area at risk of MI SVF compared to MI only. Infarcted LV tissue displayed higher mRNA expression in Fibronectin (Fn1), Vegfa, Sdf1, Cxcr4, Nos3 (eNOS) and Tbxa2r when treated with SVF construct at time of infarct compared to MI only. N≥5 rats/group, values are mean±SE.

Prior art cardiac patches implanted after MI are known to attenuate the reduction in overall heart function compared to untreated hearts. Therefore, we wanted to determine if our SVF construct impacted overall LV function in a similar manner. PV relationships were acquired after 4 weeks of treatment and are displayed in FIG. 5A. The PV relationship was clearly shifted to the right in MI and MI Vicryl animals, due mainly to an increase in both ESV and EDV compared to Sham and MI SVF groups. EF was significantly decreased in MI and MI Vicryl by ~50% in both groups compared to Sham and MI SVF. Similar values existed between all groups in parameters such as HR, ESP, EDP, and SV (FIG. 5B).

Regional Microvascular Perfusion and Function after Construct Implantation

Figure 3A:
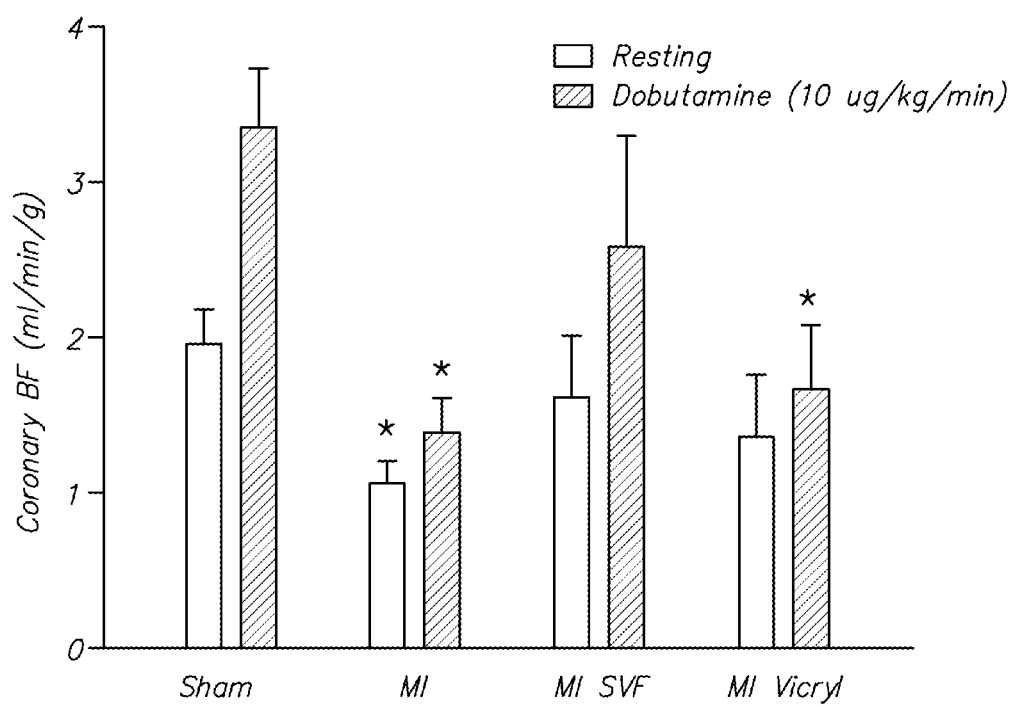
FIG. 3A shows mean coronary BF in area at risk during baseline and dobutamine conditions. An asterisk (*) indicates significantly different from corresponding BF condition in Sham.
Figure 3B:
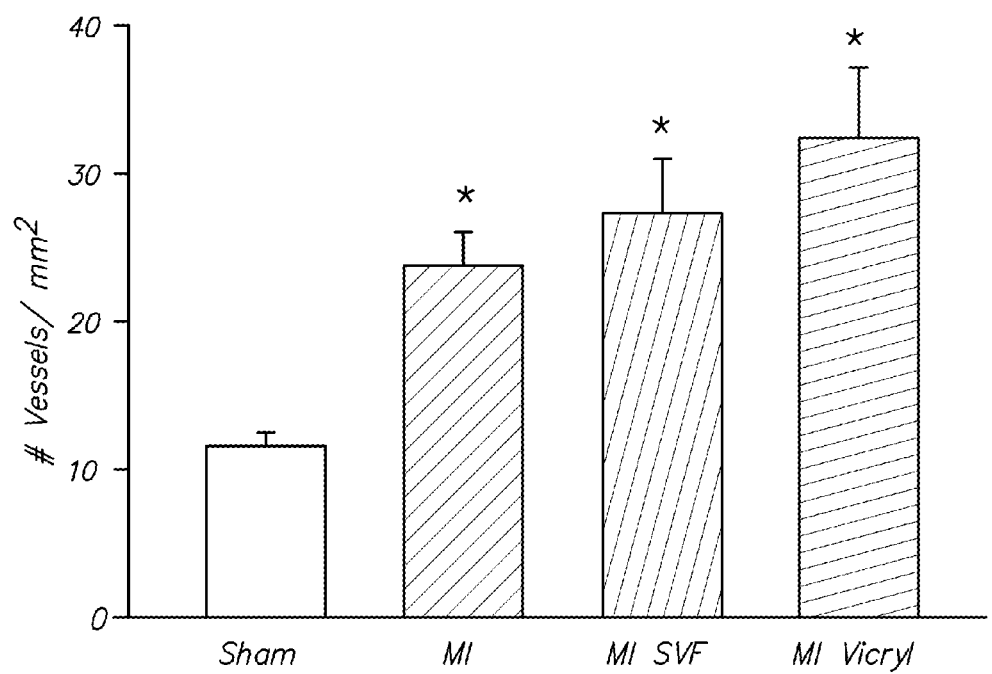
FIG. 3B shows vessel count was significantly higher in all MI groups compared to Sham. An asterisk (*) indicates significantly different from Sham.
Figure 3C:
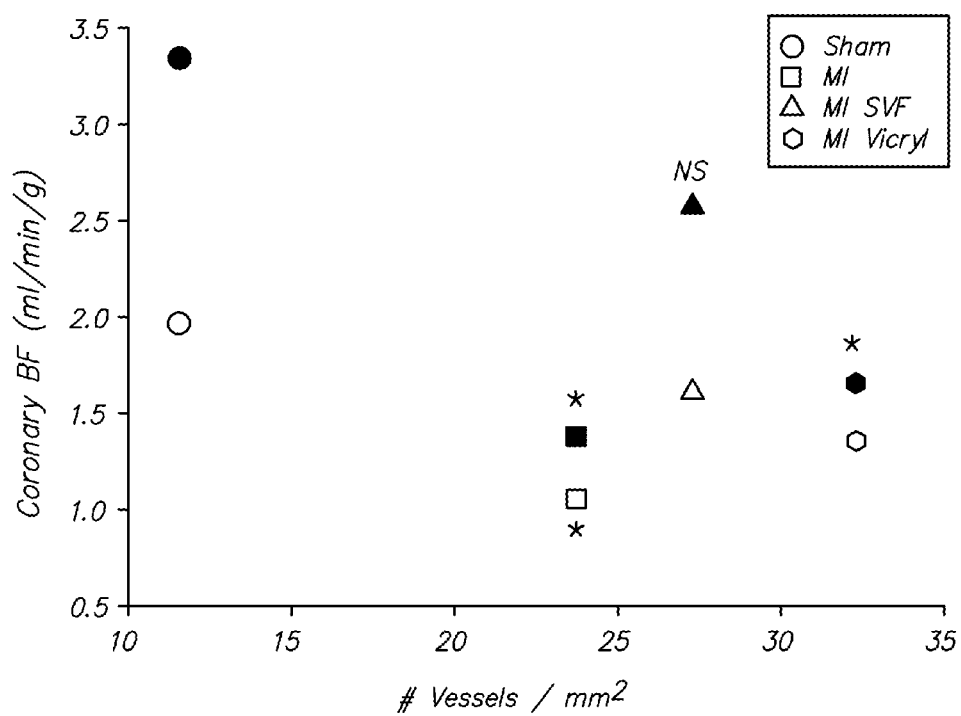
FIG. 3C shows average BF perfusion during baseline (open symbols) and dobutamine infusion (closed symbols) versus the average number of vessels/mm$^2$ in the area at risk. Despite increased number of vessels in all MI groups, MI only exhibited lower baseline BF compared to Sham. Similarly, maximal perfusion in the infarcted region was lower in both MI and MI Vicryl compared to Sham. Variance is not presented in figure in order to emphasize differences between groups. An asterisk (*) indicates significant difference from corresponding BF condition in Sham.
Figure 3D:
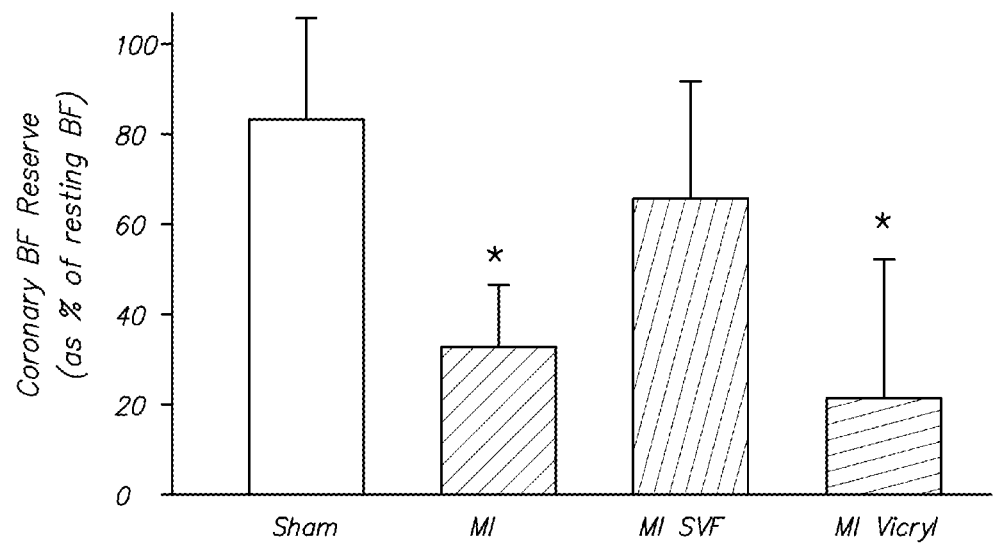
FIG. 3D shows coronary BF reserve expressed as % of baseline BF. MI and MI Vicryl have significantly lower coronary BF reserve than Sham. There was no statistical difference between Sham and MI SVF. An asterisk (*) indicates significant difference from Sham. Values are mean±SE (except in C). N≥7 rats/group, P≤0.05.
Figure 4A:
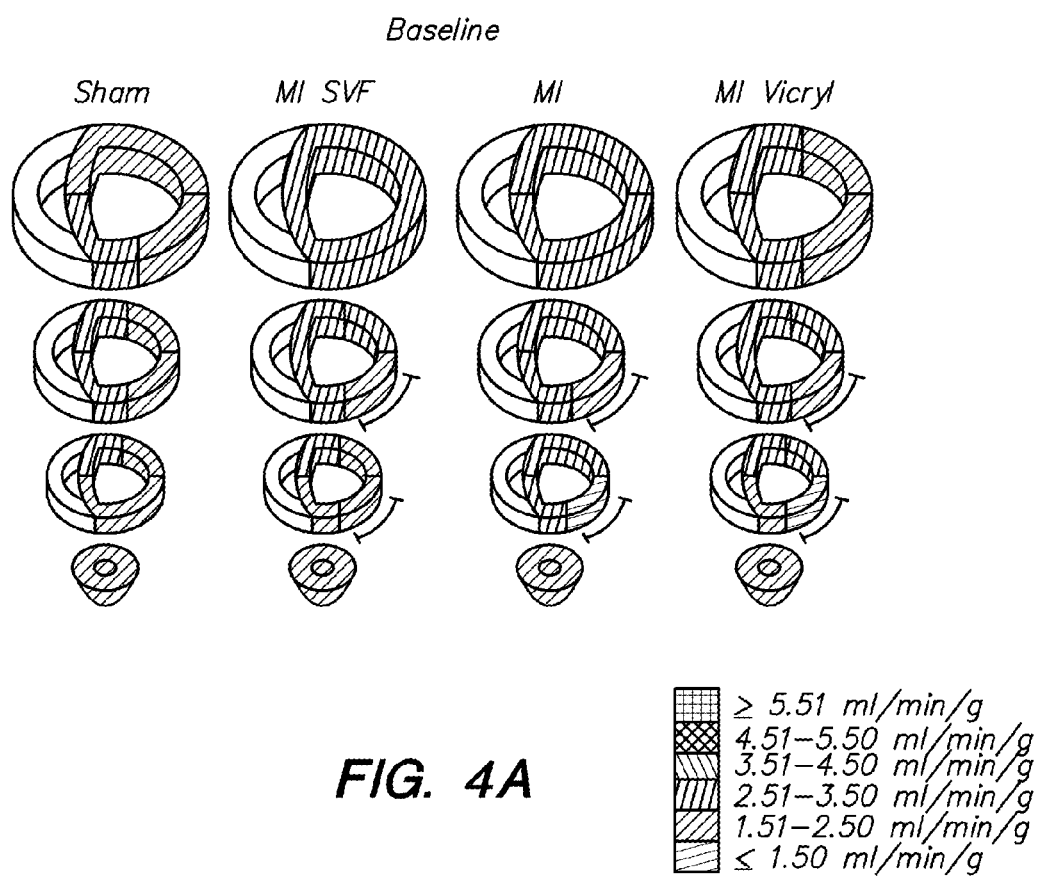
FIG. 4 shows average LV blood flow (ml/min/g), evaluated by the injection of two different stable isotope labeled microspheres during baseline and dobutamine infusion. After explant, LV rings above the apex were quartered, and area at risk is indicated by the braced lines in each of the MI groups. Blood perfusion in the area at risk is similar between sham and MI SVF during both baseline and dobutamine conditions (N≥7 rats/group).
Figure 4B:
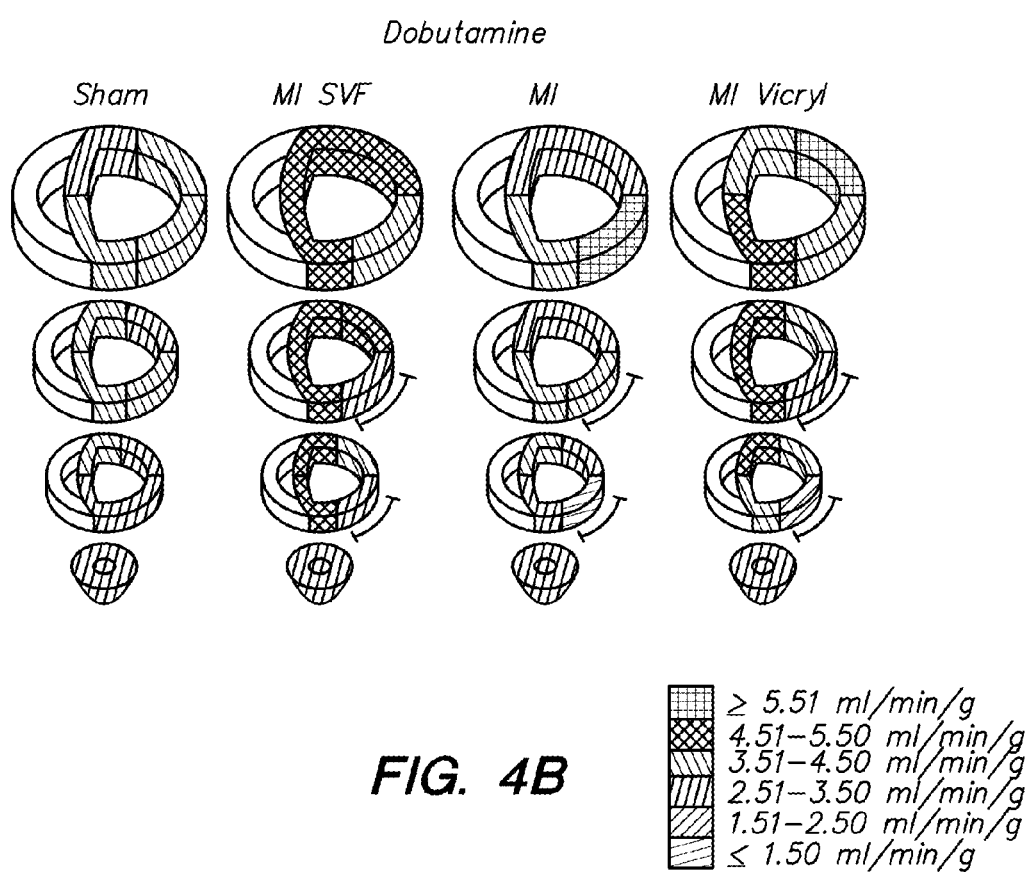

Further evaluation was conducted to determine if BF perfusion to the microcirculation, and specifically in the area of infarct, was associated with assessment of overall heart function in all groups. Following infusion of microspheres, BF was determined in 4 radial slices from the apex to papillary muscle, and all but the apex was quartered. Quartering the radial slices allowed us to analyze BF in the area at risk, peri-infarct, septal wall, and non-infarcted LV wall. Implantation of an SVF-laden construct following MI sustained overall microcirculatory perfusion in the area of infarct during both baseline and dobutamine infusion to levels exhibited by sham-control rats 4 weeks post-surgery (FIGS. 4 and 3A). FIG. 4 shows the overall blood flow changes in and around the area at risk for all groups during both baseline and dobutamine conditions. MI only and MI Vicryl groups were associated with a 46% and 31% decline (respectively) in baseline blood flow to the area of infarct compared to Sham, and this was significant in MI only rats. Compared to Sham rats, this deficiency persisted in MI and MI Vicryl when challenged with dobutamine, resulting in approximately 55% less perfusion in the infarct region in both groups. There was no statistical difference in dobutamine-induced absolute BF between Sham and MI SVF (FIG. 3A). Additionally, coronary BF reserve was sustained in the MI SVF hearts (FIGS. 3C&D). MI and MI Vicryl exhibited significantly decreased coronary BF reserve compared to Sham rats (61% and 75% decline, respectively, FIG. 3D). To determine if the increase in blood perfusion was associated with an increase in the amount of vessels in the infarct area, we counted GS-1+ vascular elements from all groups (average of 5 fields/heart). FIG. 3B displays higher GS-1+ count in the infarcted region of all MI groups compared to both sham.

Cell Engraftment

Figure 2:
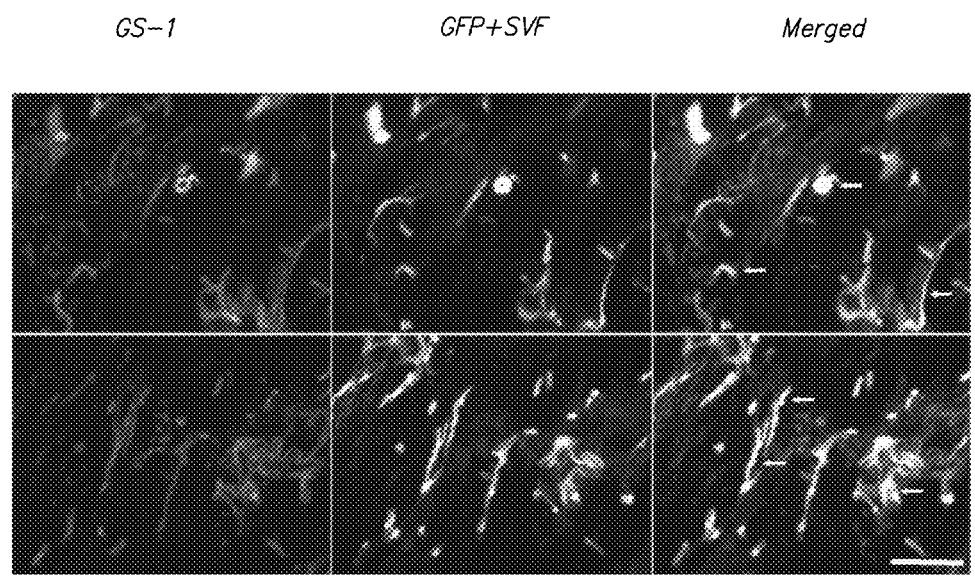
FIG. 2 shows an immunohistochemistry of MI SVF hearts. Four weeks after MI and GFP+SVF construct implantation, GS-1 (left column) was used to identify endothelial cell-comprised vessels in red, while GFP+SVF elements were detected by anti-GFP antibody in green (middle column). Merged images show engrafted GFP+SVF elements persist up to four weeks after implant in epicardial vessels in the area of repairing infarct (arrows, right column). Scale bar=100 μm.

Four weeks after MI and SVF construct implantation, immunohistochemistry staining revealed the presence of engrafted GFP+SVF elements in the area of infarct (FIG. 2, middle). The grafted cells were detected by anti-GFP immunostaining. In addition, endothelial cell-comprised vessels were identified through GS-1 staining (FIG. 2, left). Merged GFP and GS-1 images suggest that implanted GFP+SVF cells had migrated into the infarct area and specifically formed de novo vessels or located around existing vascular elements within the myocardium (FIG. 2, right)

Discussion

A cardiac construct can be utilized for the treatment of myocardial ischemia by targeting the coronary microcirculation. First, we created a three-dimensional adipose SVF cell construct that can be implanted on the epicardium after MI. Second, while all MI groups exhibited an increase in microvessel density in the area of infarct compared to Sham, only MI hearts treated with the SVF construct exhibited sustained coronary BF reserve four weeks following infarct. Third, clinical indices of overall heart function, such as EF, ESV and EDV were significantly improved in MI SVF animals compared to MI and MI Vicryl. Lastly, engraftment of GFP+SVF cells was detected around vessels in the myocardium four weeks following MI and SVF construct implant. These data indicate that the SVF construct implanted immediately following MI not only maintained favorable cardiac function following MI, but also protected the coronary microcirculation in the area of infarct to allow sustained coronary BF. The SVF construct is one of the first successful potentially autologous therapies shown to promote the development and/or maintenance of an ischemic and injured coronary microvasculature. The clinical potential of an autologous construct made from adipose-derived SVF is high, as the SVF construct may serve not only as a superior therapy in promoting microvessel survival and/or growth of new vessels following coronary infarct, but also could be utilized in restoring microcirculation to ischemic tissue in a variety of cardiomyopathies.

All MI groups demonstrated an increased number of GS-1+ vessels in the area at risk (FIG. 3B), but only the MI SVF group realized improved coronary BF (FIG. 3A). Preliminary data from our laboratory has shown adipose-derived SVF cells are capable of forming a de novo microvasculature and migrating into the vessel wall of existing neovessel segments to assemble parts of the vasculature (data not shown). It is likely that implantation of the SVF construct following MI promotes a stable angiogenic environment, and helps accomplish functional neovascularization in the infarct region. Once SVF construct cells have migrated into the vascular network of infarcted tissue (FIG. 2), existing vessels in MI SVF hearts may thrive due to secreted paracrines from the implanted SVF cells, as cells on the SVF construct exhibited an increase in relative gene expression associated with angiogenesis (FIG. 7A). Others have also pointed to this potential paracrine mechanism. A dermal fibroblast construct (3DFC), similar to the SVF construct used in the present study, has also exhibited increased gene expression of angiogenesis-related growth factors, such as HGF and VEGF. Additionally, intracardiac injection of fat-derived stromal cells (lacking the vascular elements included in the present study) mediated improvement of myocardial regeneration through the secretion of a wide spectrum of angiogenic factors, such as VEGF, HGF, and Ang-1. Therefore, it's likely the cells on the SVF construct migrate and stabilize the repairing vessels in the infarct region by the secretion of angiogenic factors following an MI.

Traditional therapies to address cardiac ischemia have focused primarily upon restoring patency to occluded, upstream coronary arteries. However, reopening the occluded or stenotic coronary artery does not necessarily translate into improved cardiac perfusion in all clinical cases, despite angiographic evidence that the blockage was removed or bypassed. This phenomenon is known as no-reflow, and between 3.2-48% of patients with PCI-treated acute MI have shown this impairment of distal microcirculatory function without obstruction to blood flow. See Feldman et al., Reperfusion syndrome: relationship of coronary blood flow reserve to left ventricular function and infarct size, *J Am Coll Cardiol* 35: 1162-1169, 2000; Resnic F S et al., No-reflow is an independent predictor of death and myocardial infarction after percutaneous coronary intervention, *Am Heart J* 145: 42-46, 2003. Resnic et al. recently demonstrated that in patients undergoing PCI, those that developed this microcirculatory dysfunction following the procedure had a fivefold increased risk of MI and fourfold increased risk of death. No reflow is a powerful predictor of death or MI even after multivariable analysis. Therefore, treatment with a SVF construct in addition to traditional therapies may arrest dysfunctional microcirculation and redirect beneficial coronary microvascular repair in a broad spectrum of cardiac conditions.

To completely assess the microvasculature, one needs to examine both structure and function. Measuring coronary flow reserve (CFR) can assess both the structural and functional integrity of the microvasculature, and is measured clinically through the use of a Doppler-tipped guidewire during both baseline and during hyperemic flow through a bolus injection of adenosine. Diminished CFR provides information about the ability of compensatory mechanisms for vasodilatory function of the myocardium. CFR is correlated with the amount of viable myocardium following acute MI, LV systolic function, EF and in-hospital adverse cardiac events. In addition, auspicious microvascular function during the convalescent stage after MI may positively affect remote stage functional and morphological outcomes of the LV. Furthermore, the degree of microvascular damage following acute MI correlates with infarct size and subsequent functional recovery. Therefore, it is clinically significant according to the present disclosure that post-MI treatment with the SVF construct sustained coronary BF reserve (measured by dobutamine infusion) to Sham levels, indicating that the microvasculature present in the infarct region of the myocardium can remain functional following MI and adequately provide tissue perfusion during increased myocardial demand.

Simply demonstrating intact microvessels does not imply functional integrity of these vessels, particularly after MI. Surprisingly, an increased number of vessels have been found in the infarct area in all MI groups compared to Sham (FIG. 3B). However, when this data is compared against microvascular BF, it becomes apparent that simply demonstrating increased vessel counts does not necessarily translate into microvascular function, as MI and MI Vicryl were deficient in coronary BF reserve (FIG. 3C). Future studies evaluating post-MI, proangiogenic therapies should be prepared to not only assess sum vessel count, but also to measure vascular function. Based on our current results, the SVF construct is ideal for proangiogenic therapy that results in not only increased number of microvessels, but functional microvascular perfusion to the area of infarct.

Although the current study demonstrates that implantation of a SVF construct immediately following coronary occlusion leads to favorable structural and functional outcomes, we realize that more clinically relevant time point studies should be performed regarding therapeutic timing post-MI. We chose to implant the SVF construct immediately following MI in order to focus directly on the microvascular effects of the SVF construct in an area of acute ischemia. Our approach allowed us to avoid the complications of progressive, and sometimes irreversible pathological changes that occur weeks or even months following a MI, such as cellular necrosis, scar tissue formation, and thinning of outer LV wall. Along those lines, others have previously shown that an epicardial construct consisting of progenitor and muscle cells implanted 30-days post-MI can still lead to improved angiogenesis and cell survival. Therefore, if we expand the tissue-engineered focus to incorporate muscle cells into the SVF construct, we could potentially strengthen the integrity of the construct and assist with global LV contractile changes that occur after chronic MI. Additionally, a catheter-based delivery of our SVF construct would certainly maximize its therapeutic and clinical potential. This would allow the utilization of the SVF construct during more frequently performed and preferred closed chest procedures compared to open chest surgeries.

In summary, we have shown that therapeutic treatment with the SVF construct following acute MI results in greater microvascular perfusion to the area of infarct 4 weeks following occlusion. Presumably, improved microcirculatory function prevented infarct progression thereby preserving overall cardiac function. Favorable microvascular status may be linked with increased viable myocardium following acute MI, LV systolic function, improved EF and a decrease in in-hospital adverse cardiac events. It is important to note that the SVF construct therapy is fully autologous and adipose serves as an abundant, surgically accessible, and regenerative cell-rich source. With some minor changes the SVF construct is amenable to a number of delivery approaches including catheter-based procedures as a provascular therapy in many types of ischemic and infarcted conditions, including angina, no-reflow, and coronary microvascular dysfunction.

While embodiments and applications have been shown and described, it would be apparent to those skilled in the art having the benefit of this disclosure that many more modifications than mentioned above are possible without departing from the inventive concepts disclosed herein. The invention, therefore, and the scope of the appended claims, should not be limited to the embodiments described herein.

What is claimed is:

1. A method for preparing a three dimensional tissue construct for use in treating a patient, comprising:
    isolating adipose-derived stromal vascular fraction cells from a sample of adipose tissue;
    plating the cells into a polymer scaffold; and
    culturing the plated scaffold for at least 14 days in a culture solution comprising DMEM with between approximately 5% and approximately 20% FBS, wherein immediately after culturing for 14 days, at least about 70% of the cells are positive for a CD68 marker.

2. The method of claim 1, wherein the scaffold comprises polyglycolic acid.

3. The method of claim 2, wherein the step of isolating comprises:
    digesting the adipose tissue in a collagenase solution;
    separating adipocytes from the digested adipose tissue to create a cell pellet; and
    suspending the cell pellet in a solution comprising bovine serum albumin.

4. The method of claim 1, wherein the culture solution comprises between approximately 8% and approximately 12% FBS.

5. The method of claim 1, wherein the culture solution comprises about 10% FBS.

6. The method of claim 1, wherein the adipose tissue is obtained by liposuction.

7. A method for treating an animal suffering from acute myocardial infarction, the animal comprising an infarct region comprising an epicardial surface, comprising:
    preparing a three dimensional tissue construct according to claim 1; and
    suturing the construct directly onto the epicardial surface.

8. The method of claim 7, wherein the step of suturing takes place within 12 hours of the onset of the acute myocardial infarction.

9. The method of claim 8, wherein the step of suturing takes place within 8 hours of the onset of the acute myocardial infarction.

10. The method of claim 8, wherein the step of suturing takes place within 4 hours of the onset of the acute myocardial infarction.

11. The method of claim 7, wherein the animal is a human.

12. The method of claim 11, wherein the adipose tissue is obtained from the human.

13. The method of claim 7, wherein the step of suturing comprises covering the site of an infarct on the epicardial surface, and securing the construct to the epicardial surface.

14. The method of claim 13, wherein a single suture is used.

* * * * *